US008962328B2

United States Patent
Cho et al.

(10) Patent No.: US 8,962,328 B2
(45) Date of Patent: Feb. 24, 2015

(54) **CULTIVATION MEDIUM FOR *AGROBACTERIUM*-MEDIATED TRANSFORMATION OF DICOT PLANTS**

(75) Inventors: Hyeon-Je Cho, Fremont, CA (US); Linda A. Castle, Mountain View, CA (US); Theodore M. Klein, Wilmington, DE (US); Tai Minh, San Jose, CA (US); York Moy, San Francisco, CA (US)

(73) Assignees: Pioneer Bred International Inc, Johnston, IA (US); E.I. DuPont de Nemours, Wilmington, DE (US)

( * ) Notice: Subject to any disclaimer, the term of this patent is extended or adjusted under 35 U.S.C. 154(b) by 154 days.

(21) Appl. No.: 13/438,077

(22) Filed: Apr. 3, 2012

(65) Prior Publication Data

US 2012/0255070 A1    Oct. 4, 2012

Related U.S. Application Data

(60) Provisional application No. 61/471,431, filed on Apr. 4, 2011.

(51) Int. Cl.
| | |
|---|---|
| *C12N 5/00* | (2006.01) |
| *C12N 5/02* | (2006.01) |
| *C12N 15/82* | (2006.01) |
| *C12N 1/20* | (2006.01) |

(52) U.S. Cl.
CPC .............. *C12N 15/8205* (2013.01); *C12N 1/20* (2013.01)
USPC ............................ 435/431; 435/410; 435/420

(58) Field of Classification Search
CPC ......... A01H 4/00; C12N 15/82; C12N 5/0025

USPC .......................................... 435/410, 420, 431
See application file for complete search history.

(56) References Cited

U.S. PATENT DOCUMENTS

| | | |
|---|---|---|
| 5,416,011 A | 5/1995 | Hinchee et al. |
| 7,057,090 B1 * | 6/2006 | Zilinskas et al. ............. 800/294 |

OTHER PUBLICATIONS

Dodds et al. "Experiments in Plant Tissue Culture," 1999, Cambridge University Press, Third Edition, p. 240.*
Saharan et al. "Studies on improved *Agrobacterium*-mediated transformation in two indica rice (*Oryza sativa* L.)," African Journal of Biotechnology vol. 3, (11), pp. 572-575, Nov. 2004.*
Chu, et al.; "Establishment of an Efficient Medium for Anther Culture of Rice Through Comparative Experiments on the Nitrogen Sources"; Scientia Sinca (1975) 18(5):659-668.
Frame, et al.; "*Agrobacterium*-mediated transformation of Hi II immature zygotic embryos and recovery of transgenic maize plants"; Plant Physiology (2002) 129:13-22; Updated Feb. 24, 2005.

(Continued)

*Primary Examiner* — Susan McCormick Ewoldt
(74) *Attorney, Agent, or Firm* — Pioneer Hi-Bred Int'l, Inc.

(57) ABSTRACT

Compositions and methods are provided for the efficient transformation of a dicot plant. More particularly, compositions and methods of the present invention find use in agriculture for *Agrobacterium*-mediated transformation of a dicotyledonous plant. The compositions include cultivation media comprising high concentrations of sucrose and glucose. The cultivation media find use in methods directed to *Agrobacterium*-mediated transformation of a dicot plant with a gene of interest. In this manner, any gene of interest can be introduced into a dicot plant with high transformation efficiency and reduced tissue necrosis.

3 Claims, 3 Drawing Sheets
(3 of 3 Drawing Sheet(s) Filed in Color)

(56) References Cited

OTHER PUBLICATIONS

Aggarwal, et al.; "*Agrobacterium tumefaciens* mediated genetic transformation of selected elite clone(s) of *Eucalyptus tereticornis*"; Acta Physiol Plant (2011) 33:1603-1611.

Khanna, et al.; "*Agrobacterium tumefaciens*-mediated transformation of wheat using a superbinary vector and a polyamine-supplemented regeneration medium"; Plant Cell Rep (2003) 21: 429-436.

Saharan, et al.; "Studies on improved *Agrobacterium*-mediated transformation in two Indica rice (Oryza sativa L.)"; African Journal of Biotechnology (2004) 3(11): 572-575.

Shahin, et al.; "Transformation of Cultivated Alfalfa Using Disarmed *Agrobacterium tumefaciens*"; Crop Sci (1986) 26: 1235-1239.

Zhao, et al.; "*Agrobacterium*-mediated sorghum transformation", Plant Molecular Biology (2000) 44: 789-798.

\* cited by examiner

CULTIVATION MEDIUM FOR *AGROBACTERIUM*-MEDIATED TRANSFORMATION OF DICOT PLANTS

CROSS REFERENCE

This utility application claims the benefit U.S. Provisional Application No. 61/471,431, filed Apr. 4, 2011, which is incorporated herein by reference.

FIELD OF THE INVENTION

The present disclosure relates to the field of plant biotechnology. More particularly, the present disclosure relates to compositions and methods for *Agrobacterium*-mediated transformation of dicotyledonous plants.

BACKGROUND OF THE INVENTION

Cultivated dicotyledonous crops such as soybean, *Brassica*, and cotton have substantial commercial value throughout the world. The development of scientific methods useful in improving the quantity and quality of soybean and other crops is, therefore, of significant commercial interest. Significant effort has been expended to improve the quality of cultivated dicotyledonous crop species by conventional plant breeding. Methods of conventional plant breeding have been limited, however, to the movement of genes and traits between plant varieties.

In addition to traditional breeding techniques, incorporation of disease resistance, increased or modified oil content, and other desirable traits can be envisioned using the modern tools of molecular biology including plant genetic engineering. Plant genetic engineering involves the transfer of a desired gene or genes into the inheritable germline of crop plants such that those genes can be bred into or among the elite varieties used in modern agriculture. Gene transfer techniques allow the development of new classes of crop varieties with improved disease resistance, herbicide tolerance, and increased nutritional value.

*Agrobacterium* has been widely used for the transformation of plants. *Agrobacterium* is a soil born phytopathogen that integrates a nucleic acid molecule (i.e., T-DNA) into the genome of a large number of dicotyledonous plants. *Agrobacterium*-mediated transformation involves incubation of cells or tissues with the bacterium, followed by regeneration of plants from the transformed cells via a callus stage. The advantage of the *Agrobacterium*-mediated gene transfer is that it offers the potential to regenerate transgenic cells at relatively high frequencies without a significant reduction in plant regeneration rates. Moreover, the process of DNA transfer to the plant genome is defined. That is, the DNA does not normally undergo any major rearrangements, and it integrates into the genome often in single or low copy numbers. Inoculation of a plant tissue with *Agrobacterium* is a disruptive process that can trigger a hypersensitive response in the tissue. As a result, the target tissue may become necrotic and the overall survival rate of transformants can be limited.

Accordingly, there remains a need for improved transformation methods to promote the engineering of desirable traits into agronomically important crops. In addition, there remains a need for highly efficient transformation methods that yield regenerable plant tissue.

SUMMARY OF THE INVENTION

Compositions and methods are provided for the efficient transformation of a dicot plant. More particularly, compositions and methods of the present invention find use in agriculture for *Agrobacterium*-mediated transformation of a dicotyledonous plant. The compositions include cultivation media comprising high concentrations of sucrose and glucose. In an embodiment the cultivation medium further comprises a nitrogen source. In some embodiments the nitrogen source is selected from at least one of the group consisting of potassium nitrate, ammonium sulphate, and asparagine. The cultivation media find use in methods directed to *Agrobacterium*-mediated transformation of a dicot plant with a gene of interest. In this manner, any gene of interest can be introduced into a dicot plant with high transformation efficiency and reduced tissue necrosis. The transferred gene will be present in the transformed plant in low copy number.

The methods comprise introducing into a plant cell a polynucleotide sequence of interest by co-cultivation of the plant material with an *Agrobacterium* having the polynucleotide sequence within T-DNA borders, in a medium having high concentrations of glucose and sucrose. Expression of a coding sequence by such a transformed plant will result in the production of a polypeptide of interest in the transformed plant. Accordingly, transgenic (e.g., transformed) plant cells, plant tissues, plants and seeds thereof are also provided. The present invention also encompasses regenerating fertile transgenic plants and transgenic seeds produced therefrom, as well as T1 and subsequent generations.

The following embodiments are encompassed by the present disclosure.

1. A cultivation medium having high levels of sucrose and glucose and further comprising at least one of potassium nitrate, ammonium nitrate, and asparagine.
2. The medium of embodiment 1, wherein said high levels comprise at least 1% to about 13% (w/v) sucrose and about 2% to about 7.5% (w/v) glucose.
3. The medium of embodiment 1 or 2 and further comprising a nitrogen source.
4. The medium of embodiment 3, wherein said nitrogen source is selected from at least one of the group consisting of: potassium nitrate, ammonium nitrate, and asparagine
5. The cultivation medium of embodiments 4, comprising about 10 to about 100 grams/Liter sucrose, about 20 to about 50 grams/Liter glucose, about 2.4 grams/Liter to about 3.9 grams/Liter potassium nitrate ($KNO_3$), about 0.2 grams/Liter to about 0.6 grams/Liter ammonium sulphate (($NH_4)_2SO_4$), and about 1 gram/Liter asparagine.
6. The medium of embodiment 3, wherein said sucrose is present at about 68 grams/Liter and glucose is present at about 36 grams/Liter.
7. The cultivation medium of embodiments 1, 2, 3, 4, 5, or 6, wherein said medium has a pH of about 5 to about 7.
8. The cultivation medium of embodiment 7, wherein said medium has a pH of about 5.4 to about 5.7.
9. The cultivation medium of embodiments 1, 2, 3, 4, 5, 6, 7 or 8, further comprising casein hydrolysate.
10. The cultivation medium of embodiment 5, comprising about 68 grams/L sucrose, about 36 grams/L glucose, about 3.5 grams/L potassium nitrate ($KNO_3$), about 0.5 grams/L ammonium sulphate (($NH_4)_2SO_4$), and about 1 gram/L asparagine.
11. The cultivation medium of embodiment 10, further comprising casein hydrolysate.
12. The cultivation medium of embodiment 11, wherein said medium has a pH of about 5 to about 7.
13. The cultivation medium of embodiment 12, wherein said medium has a pH of about 5.4 to about 5.7.

14. A method for producing regenerable plant cells having a nucleotide sequence of interest, said method comprising the steps of:
 (a) contacting a tissue from a dicotyledonous plant with an *Agrobacterium* comprising a vector which comprises said nucleotide sequence, wherein said nucleotide sequence comprises at least an expression cassette comprising a gene which confers resistance to a selection agent;
 (b) co-cultivating the tissue with said *Agrobacterium* on a porous solid support in the presence of the medium of embodiments 1, 2, 3, 4, 5, 6, 7, 8, 9, 10, 11, 12, or 13;
 (c) culturing the tissue of step (b) in a medium comprising an antibiotic capable of inhibiting the growth of *Agrobacterium* and said selection agent; and
 (d) selecting regenerable cells comprising said nucleotide sequence.
15. The method of embodiment 14, wherein said tissue is embryogenic callus.
16. The method of embodiment 14, wherein said tissue is wounded.
17. The method of embodiment 16, wherein said wounded tissue is chopped or sonicated.
18. The method of embodiment 14, wherein said co-cultivating further comprises a lysozyme wash.
19. The method of embodiment 14, wherein said medium further comprises an antioxidant.
20. The method of embodiment 14, wherein said porous solid support is a filter paper or a glass fiber filter.
21. The method of embodiment 14, wherein co-cultivating further comprises culturing the tissue with said *Agrobacterium* for about 2 days to about 5 days.
22. The method of embodiment 14, wherein the contacting step takes place in a liquid suspension.
23. The method of embodiment 14, wherein the co-cultivation step takes place on a solid medium.
24. The method of embodiment 14, further comprising a resting step after the co-cultivation step.
25. The method of embodiment 24, wherein said resting step comprises culturing the tissue in a medium comprising an agent capable of inhibiting the growth of *Agrobacterium*.
26. The method of embodiment 25, wherein said agent is selected from the group consisting of cefotaxime, timetin, vancomycin, and carbenicillin.
27. The method of embodiment 14, wherein said regenerated transformed soybean plant is a fertile transformed soybean plant.
28. The method of embodiment 14, wherein at least about 70% of tissue following the co-cultivation step is non-necrotic.
29. The method of embodiment 14, wherein tissue necrosis following the co-cultivation step is reduced relative to necrosis present in tissue co-cultivated with an *Agrobacterium* in the absence of the medium of embodiments 1, 2, 3, 4, 5, 6, 7, 8, 9, 10, 11, 12, or 13.
30. A method for transforming a soybean plant with a nucleotide sequence of interest, said method comprising the steps of:
 (a) contacting a tissue from a soybean plant with an *Agrobacterium* comprising a vector, said vector comprising said nucleotide sequence of interest and further comprising a second nucleotide sequence which confers resistance to a selection agent;
 (b) co-cultivating the tissue of step (b) with said *Agrobacterium* on a porous solid support in the presence of the medium of embodiments 1, 2, 3, 4, 5, 6, 7, 8, 9, 10, 11, 12, or 13;
 (c) culturing the tissue in a medium comprising an antibiotic capable of inhibiting the growth of *Agrobacterium* and said selection agent; and
 (d) regenerating a transformed soybean plant.
31. The method of embodiment 30, wherein said tissue is embryogenic callus.
32. The method of embodiment 30, wherein said tissue is wounded.
33. The method of embodiment 32, wherein said wounded tissue is chopped.
34. The method of embodiment 30, wherein said co-cultivating further comprises a lysozyme wash.
35. The method of embodiment 30, wherein said medium further comprises an antioxidant.
36. The method of embodiment 30, wherein said porous solid support is a filter paper or a glass fiber filter.
37. The method of embodiment 30, wherein co-cultivating further comprises culturing the tissue with said *Agrobacterium* for about 2 days to about 5 days.
38. The method of embodiment 30, wherein the contacting step takes place in a liquid suspension.
39. The method of embodiment 30, wherein the co-cultivation step takes place on a solid medium.
40. The method of embodiment 30, further comprising a resting step after the co-cultivation step.
41. The method of embodiment 40, wherein said resting step comprises culturing the tissue in a medium comprising an agent capable of inhibiting the growth of *Agrobacterium*.
42. The method of embodiment 41, wherein said agent is selected from the group consisting of cefotaxime, timetin, vancomycin, and carbenicillin.
43. The method of embodiment 30, wherein said regenerated transformed soybean plant is a fertile transformed soybean plant.
44. The method of embodiment 30, wherein at least about 70% of tissue following the co-cultivation step is non-necrotic.
45. The method of embodiment 30, wherein tissue necrosis following the co-cultivation step is reduced relative to necrosis present in tissue co-cultivated with an *Agrobacterium* in the absence of the medium of embodiments 1, 2, 3, 4, 5, 6, 7, 8, 9, 10, 11, 12, or 13.

BRIEF DESCRIPTION OF THE DRAWINGS

This patent or application file contains at least one drawing figure executed in color. Copies of this patent or patent application publication with color drawing(s) will be provided by the Office upon request and payment of the necessary fee.

DETAILED DESCRIPTION

Provided are compositions and *Agrobacterium*-mediated methods for transforming dicotyledonous plants. Compositions include cultivation media comprising high concentrations of sucrose and glucose. Compositions further comprise at least one nitrogen source selected from potassium nitrate, ammonium sulphate, and asparagine. The cultivation media of the present invention find use in methods directed to *Agrobacterium*-mediated transformation of a dicot plant with a gene of interest. In this manner, any gene of interest can be introduced into a dicot plant with high transformation efficiency and reduced tissue necrosis. The transferred gene will be present in the transformed plant in low copy number. Transformed plants, plant cells, and seeds are also disclosed herein.

In the description that follows, a number of terms are used extensively. The following definitions are provided to facilitate understanding of the invention.

Compositions

Compositions provided herein include cultivation media having high levels of sucrose and glucose. By "high levels" is intended that the composition comprises at least 1% (w/v) sucrose and at least 2% (w/v) glucose. In some embodiments, a cultivation medium for *Agrobacterium*-mediated transformation can have, for example, at least 1% to about 13% (w/v) sucrose and at least about 2% to about 7.5% (w/v) glucose. In some embodiments the cultivation medium comprises a combined sucrose and glucose concentration of less than about 21% (w/v). In some embodiments, sucrose is present at about 68 grams/Liter and glucose is present at about 36 grams/Liter.

Compositions provided herein may further comprise a nitrogen source. In some embodiments the nitrogen source is at least one of potassium nitrate, ammonium nitrate, and asparagine. Particular examples include cultivation media having about 10 to about 100 grams/Liter, about 20 to about 90 grams/Liter, about 30 to about 80 grams/Liter, about 40 to about 70 grams/liter of sucrose; about 20 to about 50 grams/Liter, about 25 to about 45 grams/Liter, about 30 to about 40 grams/Liter of glucose; about 2.0 to about 4.5 grams/Liter, about 2.4 to about 3.9 grams/Liter, about 3.0 to about 3.5 grams/Liter of potassium nitrate ($KNO_3$); about 0.1 to about 1.0 grams/Liter, about 0.2 to about 0.6 grams/Liter of ammonium sulphate (($NH_4$)$_2SO_4$); and about 0.5 to about 1.5 gram/Liter; about 1 gram/Liter of asparagine. For example, a cultivation medium can include about 60 grams/Liter, about 65 grams/Liter, about 66 grams/Liter, about 67 grams/Liter, about 68 grams/Liter, about 69 grams/Liter, about 70 grams/Liter sucrose; about 30 grams/Liter, about 35 grams/Liter, about 36 grams/Liter, about 37 grams/Liter, about 38 grams/Liter glucose; about 3.0 grams/Liter, about 3.4 grams/Liter, about 3.5 grams/Liter, about 3.6 grams/Liter, about 3.7 grams/Liter potassium nitrate ($KNO_3$); about 0.4 grams/Liter, about 0.5 grams/Liter, about 0.6 grams/Liter ammonium sulphate (($NH_4$)$_2SO_4$); and about 0.8 grams/Liter, about 0.9 grams/Liter, about 1 gram/Liter, about 1.1 grams/Liter, about 1.2 grams/Liter asparagine. In one embodiment, a cultivation media contains about 68 grams/Liter sucrose, about 36 grams/Liter glucose, about 3.5 grams/Liter potassium nitrate ($KNO_3$), about 0.5 grams/Liter ammonium sulphate (($NH_4$)$_2SO_4$), and about 1 gram/Liter asparagine. In some embodiments the molar ratio of potassium nitrate ($KNO_3$) to ammonium sulfate (($NH_4$)$_2SO_4$ is about 8:1 to about 10:1. In some embodiments the molar ratio of potassium nitrate ($KNO_3$) to ammonium sulfate (($NH_4$)$_2SO_4$ is about 9:1.

A cultivation medium provided herein may further comprise any other appropriate constituents including, without limitation, antioxidants, vitamins (e.g., $B_5$ vitamins), salts, sorbitol, mannitol, maltose, magnesium chloride, casein hydrosylate, activated charcoal, acetosyringone, and agar.

Methods of Using Compositions

In another aspect, a method for transforming a dicotyledonous plant, plant tissue, or plant cell is provided. The methods provided herein rely upon the use of *Agrobacterium*-mediated gene transfer to produce regenerable plant cells having a nucleotide sequence of interest. *Agrobacterium*-mediated gene transfer exploits the natural ability of *Agrobacterium tumefaciens* to transfer DNA into plant chromosomes. *Agrobacterium* is a plant pathogen that transfers a set of genes encoded in a region called T-DNA of the Ti plasmid into plant cells at wound sites. The typical result of gene transfer is a tumorous growth called a crown gall in which the T-DNA is stably integrated into a host chromosome. The ability to cause crown gall disease can be removed by deletion of the genes in the T-DNA without loss of DNA transfer and integration. The DNA to be transferred is attached to border sequences that define the end points of an integrated T-DNA.

As used herein, "plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores. The term "plant tissue" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

As used herein, the term "regenerable plant cells having a nucleotide sequence of interest" refers to plant cells in which a genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

In some embodiments, methods for producing regenerable plant cells having a nucleotide sequence of interest can include the steps of:

(a) contacting a tissue from a dicotyledonous plant with an *Agrobacterium* comprising a vector which comprises the nucleotide sequence, where the nucleotide sequence comprises at least an expression cassette comprising a gene which confers resistance to a selection agent;

(b) co-cultivating the tissue with said *Agrobacterium* on a porous solid support in the presence of a cultivation medium provided herein;

(c) culturing the tissue of step (b) in a medium comprising an antibiotic capable of inhibiting the growth of *Agrobacterium* and the selection agent; and (d) selecting regenerable cells comprising the nucleotide sequence.

In the contacting step, plant tissue to be transformed can be contacted to an *Agrobacterium*. As used herein, the term "tissue" is intended to include a plant tissue such as embryogenic callus, immature and mature embryo, immature and mature seed, meristem, cell clusters, scutella, nodes, young leaf bases, hypocotyl explants, roots, inflorescences, suspension cultures, cultures of suspended cell aggregates, meristematic regions, leaves, green tissue, non-green tissue, somatic embryos and shoot apexes and the like. As known to one skilled in the art, tissue may be obtained from any number of sources. For example, embryos can be obtained from the fertilized reproductive organs of a mature dicotyledonous plant. Embryogenic suspension cultures can be used for transformation. See, for example, Finer and Naganawa, (1998) *Plant Cell Tissue Org. Cult.* 15:125-136 and Samoylov, et al., (1998) *In Vitro Cellular and Developmental Biology—Plant* 34:8-13, both of which are herein incorporated by reference.

A variety of *Agrobacterium* species are known in the art, particularly for dicotyledon transformation. Such *Agrobacterium* can be used in the methods of the invention. See, for example, Hooykaas (1989) *Plant Mol. Biol.* 13:327; Smith, et al., (1995) *Crop Science* 35:301; Chilton, (1993) *Proc. Natl. Acad. Sci. USA* 90:3119; Mollony, et al., N: *Monograph Theor Appl Genet* NY, Springer Verlag 19:148, 1993 and Ishida, et al., (1996) *Nature Biotechnol.* 14:745; Komari, et al. (1996) *The Plant Journal* 10:165, herein incorporated by reference. See, also, DNA Cloning Service on the world wide web at DNA-cloning.com.

The *Agrobacterium* strain utilized in the methods of the invention is modified to contain a gene or genes of interest, or a nucleic acid to be expressed in the transformed cells. The nucleic acid to be transferred is incorporated into the T-region and is flanked by T-DNA border sequences. In the Ti plasmid, the T-region is distinct from the vir region whose functions are responsible for transfer and integration. Binary vector systems have been developed where the manipulated disarmed T-DNA carrying foreign DNA and the vir functions are present on separate plasmids. In this manner, a modified T-DNA region comprising foreign DNA (the nucleic acid to be transferred) is constructed in a small plasmid which replicates in *E. coli*. This plasmid is transferred conjugatively in a tri-parental mating into *A. tumefaciens* which contains a compatible plasmid-carrying virulence gene. The vir functions are supplied in trans to transfer the T-DNA into the plant genome. Such binary vectors are useful in the practice of the present invention.

A vector comprising the nucleic acid of interest is introduced into an *Agrobacterium*. The term "introduced" is intended to mean providing a nucleic acid (e.g., expression construct) or protein into a cell (e.g., *Agrobacterium*). "Introduced" includes reference to the incorporation of a nucleic acid into a eukaryotic or prokaryotic cell where the nucleic acid may be incorporated into the genome of the cell, and includes reference to the transient provision of a nucleic acid or protein to the cell. The term "introduced" includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA). General molecular techniques used in the invention are provided, for example, by Sambrook, et al., (eds.) *Molecular Cloning: A Laboratory Manual,* 1989, Cold Spring Harbor Laboratory Press, Cold Spring Harbor, N.Y.

For convenience, the nucleic acid to be transferred can be contained within DNA constructs or expression cassettes. The expression cassette or construct will comprise a transcriptional initiation region linked to the nucleic acid or gene of interest. Such an expression cassette is provided with a plurality of restriction sites for insertion of the gene or genes of interest to be under the transcriptional regulation of the regulatory regions. One or multiple expression cassettes or DNA constructs can be used in the practice of the invention.

The transcriptional initiation region, the promoter, may be native or homologous or foreign or heterologous to the host, or could be the natural sequence or a synthetic sequence. By foreign is intended that the transcriptional initiation region is not found in the wild-type host into which the transcriptional initiation region is introduced. As used herein a chimeric gene comprises a coding sequence operably linked to transcription initiation region which is heterologous to the coding sequence.

The transcriptional cassette will include the in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., 1989) *Nucleic Acids Res.* 17:7891-7903; Joshi, et al., (1987) *Nucleic Acid Res.* 15:9627-9639.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, et al., (1989) *PNAS USA,* 86:6126-6130); potyvirus leaders, for example, TEV leader (Tobacco Etch Virus) (Allison, et al., (1986); MDMV leader (Maize Dwarf Mosaic Virus); *Virology,* 154:9-20) and human immunoglobulin heavy-chain binding protein (BiP), (Macejak and Sarnow, (1991) *Nature,* 353:90-94; untranslated leader from the coat protein mRNA of alfalfa mosaic virus (AMV RNA 4), (Jobling and Gehrke, (1987) *Nature* 325:622-625; tobacco mosaic virus leader (TMV), (Gallie, et al., (1989) *Molecular Biology of RNA*, pages 237-256 and maize chlorotic mottle virus leader (MCMV) (Lommel, et al., (1991) *Virology* 81:382-385). See also, Della-Cioppa, et al., (1987) *Plant Physiology,* 84:965-968. Other methods known to enhance translation can also be utilized, for example, introns, and the like.

The expression cassettes may contain one or more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. (See, DeBlock, et al., (1987) *EMBO J.* 6:2513-2518; DeBlock, et al., (1989) *Plant Physiol.* 91:691-704; Fromm, et al., (1990) 8:833-839; Gordon-Kamm, et al., (1990) 2:603-618). For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Many selectable markers are known in the art and can be used in the practice of the invention.

Where appropriate, the selectable marker genes and other gene(s) and nucleic acid of interest to be transferred can be synthesized for optimal expression in a dicot (e.g., soybean). That is, the coding sequence of the genes can be modified to enhance expression in a dicot plant (e.g., soybean). The synthetic nucleic acid is designed to be expressed in the transformed tissues and plants at a higher level. The use of optimized selectable marker genes may result in higher transformation efficiency.

Methods for synthetic optimization of genes are available in the art. See, for example, U.S. Pat. Nos. 5,380,831; 5,436,391 and Murray, et al., (1989) *Nucleic Acids Res.* 17:477-498, herein incorporated by reference. The nucleotide sequence can be optimized for expression in soybean or alternatively can be modified for optimal expression in other dicots. The plant preferred codons may be determined from the codons of highest frequency in the proteins expressed in soybean or other dicot of interest. Likewise, the optimized sequence can be constructed using dicot-preferred codons. See, for example, Murray, et al., (1989) *Nucleic Acids Res.* 17:477-498. It is recognized that all or any part of the gene sequence may be optimized or synthetic. That is, fully optimized or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The methods disclosed herein are useful in regulating expression of any heterologous nucleotide sequence in a host plant in order to vary the phenotype of a plant. As will be evident to one of skill in the art, any nucleic acid of interest can be used in the methods of the invention. For example, a soybean plant can be engineered to express disease and insect resistance genes, genes conferring nutritional value, genes to confer male and/or female sterility, antifungal, antibacterial or antiviral genes, and the like. Likewise, the method can be used to transfer any nucleic acid to control gene expression. For example, the nucleic acid to be transferred could encode an antisense oligonucleotide.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, and commercial products.

Agronomically important traits such as oil, protein content, and the like can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109), and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432 and Mindrinos, et al., (1994) *Cell* 78:1089), and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the gat gene; see, for example, US Patent Application Publication Number 2004/0082770 and WO 2003/092360) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

The concentration of *Agrobacterium* useful in the methods of the invention may vary depending on the *Agrobacterium* strain utilized, the tissue being transformed, the plant genotype being transformed, and the like. While the concentration of *Agrobacterium* may vary, generally a concentration range of about $1 \times 10^3$ cfu/ml to about $1 \times 10^{10}$ cfu/ml, preferably within the range of about $1 \times 10^3$ cfu/ml to about $1.5 \times 10^9$ cfu/ml, and still more preferably at about $0.5 \times 10^9$ cfu/ml to about $1.0 \times 10^9$ cfu/ml, will be utilized.

In some cases, the tissue to be contacted with *Agrobacterium* is embryogenic callus. Embryogenic callus can originate in any appropriate tissue of the dicot plant. Preferably, tissue utilized in initiating callus is immature tissue such as immature embryos, immature inflorescences, and the basal portion of young leaves. For example, primary or secondary embryogenic callus can be excised from immature cotyledons. In some cases, the tissue can be wounded or chopped prior to or simultaneously with contact to *Agrobacterium*. For example, plant tissue can be wounded by chopping, cutting, or some other means prior to contacting the tissue with an *Agrobacterium* comprising a vector which comprises the nucleotide sequence of interest.

The plant tissue is co-cultivated with *Agrobacterium* in the presence of a culture medium provided herein. As used interchangeably herein, "co-cultivating", "co-cultivation" and "co-culture" refer to incubating *Agrobacterium*-contacted/infected plant tissue in the presence of the cultivation medium described herein to allow continued T-DNA delivery from *Agrobacterium* into plant cells.

In some embodiments, co-cultivation of plant tissue with *Agrobacterium* can take place on a porous solid support in the presence of the cultivation medium of the invention. For example, co-cultivation can take place with plant tissue to be transformed placed on a porous solid support (e.g., filter paper, glass fiber filter). Any appropriate porous solid support that prevents *Agrobacterium* overgrowth and retains moisture and nutritional elements can be used according to the methods provided herein. Exemplary porous solid supports can include VWR grade 415 filter paper, Whatman grade 1 filter paper, and VWR grade 693 glass fiber filters.

Embryogenic callus or other plant tissue can be positioned in any appropriate orientation for co-cultivation in the presence of the cultivation medium. By way of example, and without limitation, embryos can be positioned axis down.

The embryos or other plant tissue can be co-cultivated with the *Agrobacterium* for about 1-30 days, preferably about 2-20 days and more preferably about 3-10 days.

In some embodiments, the methods provided herein can further include the step of culturing the tissue (e.g., embryogenic callus) for a length of time prior to the co-cultivation step in a pre-culturing step. "Pre-culturing" and "pre-cultured" as used herein means culturing the cells or tissues in an appropriate pre-culture medium to support plant tissue growth prior to the introduction of a nucleic acid. In some embodiments, tissue is pre-cultured for several days (e.g., about 2 days, about 3 days, about 4 days, about 5 days, or more). Pre-culturing the plant cells may be performed using any method known to one ordinarily skilled in the art. In some cases, pre-culturing can be performed in a cultivation medium containing high levels of sucrose and glucose as provided herein.

In some cases, the methods provided herein further include a lysozyme wash step following the co-cultivation step. For example, after co-cultivation with *Agrobacterium*, plant tissue can be washed with a lysozyme-containing buffer. In some embodiments, after one or more days of co-cultivation, embryogenic cultures can be collected from the filter paper and transferred into the Petri dish containing a lysozyme-containing buffer. Embryogenic cultures can be mixed well with the lysozyme solution and incubated at room temperature, followed by removal of the lysozyme-containing buffer.

Following the co-cultivation step, the transformed cells may be subjected to an optional resting step. As used herein, "resting" refers to a culture step where plant cells, such as embryos, or other tissue, are incubated after the introduction of the nucleic acid by *Agrobacterium*-mediated infection. The resting step permits the preferential initiation and growth of callus from the transformed cells containing the nucleic acid of interest and is usually carried out in the absence of any selective pressures. The transformed plant tissue is subjected to a resting media that typically includes an antibiotic capable of inhibiting *Agrobacterium* growth. Such antibiotics are known in the art and include cefotaxime, timetin, vancomycin, carbenicillin, Plant Preservative Mixture™ (Plant Cell Technology, Inc., Washington, D.C.), and the like. Concentrations of the antibiotic will vary according to what is standard for each antibiotic. For example, concentrations of carbenicillin will range from about 50 mg/L to about 250 mg/L, carbenicillin in solid media, preferably about 75 mg/L to about 200 mg/L, and more preferably about 100-125 mg/L. Those of ordinary skill in the art of dicot transformation will recognize that the concentration of antibiotic can be optimized for a particular transformation protocol without undue experimentation.

In some embodiments, the resting phase cultures are allowed to rest in the dark at 28° C. for about 1 to about 15 days, preferably for about 3 to about 10 days, more preferably for about 5 to about 8 days. In some embodiments, conditions for the resting step can be those conditions exemplified in Example 3.

Where no resting step is used, an extended co-cultivation step can be used to provide a period of culture time prior to the addition of a selective agent for the transformed cells.

The methods provided herein further include selecting regenerable cells comprising a nucleotide sequence of interest. "Selecting" as used herein refers to the culture step in plant transformation where the transformed cells that have received and are expressing a selection marker from the introduced nucleic acid are selected. Following the co-cultivation step, or following the resting step, where it is used, the transformed cells can be exposed to selective pressure to select for those cells that have received and are expressing polypeptide from the heterologous nucleic acid introduced by *Agrobacterium*. In some cases, cells may be exposed to a selective pressure in order to favor those cells that express the selection marker and may include the use of a selective agent that allows for selection of transformants containing at least one selection marker insert. For example, where the cells are embryos, the embryos can be transferred to plates with solid medium that includes both an antibiotic to inhibit growth of the *Agrobacterium* and a selection agent. The selection agent used to select for transformants will select for preferential growth of explants containing at least one selectable marker insert positioned within the super binary vector and delivered by the *Agrobacterium*.

As indicated above, any suitable selection marker may be used including, without limitation, bar, pat, gat, PMI, hpt, nptII and positive and/or negative selectable markers and visible selection marker genes such as DS-RED, GFP, YFP, GUS and the like. Any suitable selective agent may be used including, without limitation, herbicides, such as, bialaphos, glufosinate-NH4 (PPT), sugar, such as mannose, and antibiotics such as hygromycin B or G418, and the like. During the selecting step, dead and necrotic tissues can be discarded, and green shoots and shoot buds can be subcultured to fresh medium containing the selection agent.

Selecting may optionally be carried out in light, dim, or dark conditions. The length of exposure of the plant cell to light, dim, or dark conditions may vary based in part on the type of plant species and genotype being transformed. Preferably, plant cells are rested and selected in dark conditions. In some embodiments, conditions for the selection step can be those conditions exemplified in Example 3.

After transformed plant tissue has been identified and selected, the transformed tissue can be regenerated into whole plants. Any appropriate method of regenerating whole plants can be used. The regeneration, development, and cultivation of plants from various transformed explants are well known in the art. See, for example, McCormick et al. (1986) *Plant Cell Reports* 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. In some cases, transformed embryogenic callus tissue or other transformed plant tissue can be subcultured at regular or irregular intervals in the same medium. Transgenic embryos and seeds are similarly regenerated. Individual calli can be individually separated to ensure that only one whole plant is regenerated per callus and, therefore, that all regenerated plants are derived from independent transformation events. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

The methods and compositions provided herein can be used to produce regenerable plant cells with reduced incidence of necrosis. By "reduced incidence of necrosis" is intended that transformed plant tissue exhibits fewer or smaller necrotic lesions or other indicators of plant tissue necrosis. In some cases, "reduced incidence of necrosis" can be determined relative to plant tissue transformed in the absence of a composition provided herein. Necrosis in transformed plant tissue can be detected by physically assessing the appearance of transformed tissue and, in some cases, quantifying (i.e., measuring the number and/or diameter of) necrotic lesions on the surface of the transformed tissue. For example, the extent of necrosis can be readily quantified by plant biologists and technicians through visual assessment of the area of any necrotic lesions relative to the total surface area of the plant tissue following *Agrobacterium*-mediated transformation. In some embodiments, a decrease in tissue necrosis (i.e., decrease in lesion diameter or number of lesions) can be observed in tissues transformed according to the methods provided herein. In the practice of the invention, following the co-cultivation step, necrotic lesions can, on average, account for no more than about 30% of the total area of tissue transformed according to the methods provided herein. Thus, following the co-cultivation step, non-necrotic tissue can, on average, account for more than about 70% (e.g., about 70%, about 75%, about 80%, about 85%, about 90%, about 95%, about 99%) of the total area of tissue transformed according to the methods provided herein.

The methods described herein provide for an efficient method of increasing the transformation of dicots. Any suitable dicot may be used with the methods and compositions described herein. These include, without limitation, soybean (e.g., *Glycine max*), *Brassica* spp. (e.g., *B. napus, B. rapa, B. juncea*), particularly those *Brassica* species useful as sources of seed oil, sunflower (e.g., *Helianthus annuus*), cotton (e.g., *Gossypium barbadense, Gossypium hirsutum*) or alfalfa (e.g., *Medicago sativa*) and the like.

The article "a" and "an" are used herein to refer to one or more than one (i.e., to at least one) of the grammatical object of the article. By way of example, "an element" means one or more element.

Throughout the specification the word "comprising," or variations such as "comprises," will be understood to imply the inclusion of a stated element, integer or step, or group of elements, integers or steps, but not the exclusion of any other element, integer or step, or group of elements, integers or steps.

The following examples are presented by way of illustration, and not by way of limitation.

EXPERIMENTAL

Example 1

Plant Materials and Media Compositions

The methods used to generate embryogenic suspension cultures of soybean were essentially described by Finer and Nagasawa (*Plant Cell Tiss. Org. Cult.* 15:125-136 (1988)) and Samoylov, et al., (*In Vitro Cell. Dev. Biol.-Plant* 34: 8-13 (1998)). Immature seeds less than 4 mm in length were harvested from immature soybean pods of plants grown in the greenhouse under standard conditions. The varieties of soybean used in the following examples were Jack and two elite varieties. Although these studies focused on these three varieties, the techniques can be applied to a wide range of soybean cultivars and other dicotyledonous plants. Immature seeds were surface sterilized in 10% Clorox® bleach, 0.02% Tween-20, with slight agitation for 20 minutes and then rinsed five to seven times with sterile distilled water. Immature cotyledons were aseptically excised by cutting the embryo axis off of the cotyledons and then pushing the cotyledons out of the seed coat. The cotyledons were placed (adaxial side up) on initiation media (M1) contained in a Petri plate. The Petri plates were incubated at 25° C. with 18 hour photoperiod at 60-80 $\mu E/m^2/s$ light intensity. Desirable primary or secondary embryogenic callus was excised from immature cotyledons that had been cultured on M1 for 2-5 weeks and placed into 50 ml of M2 liquid media in 250-ml flask. Liquid cultures were maintained on a rotary shaker at 150 rpm under white fluorescent and plant mixed spectrum lights at 26° C. with 18 hour photoperiod at 60-80 $\mu E/m^2/s$ light intensity. Tissue was subcultured once every week and remained in M2 liquid medium until expiration of the culture to minimize likelihood of somaclonal variation (4 months from initiation date on M2 medium). The compositions of various media used in this study are outlined in Table 1.

TABLE 1

Composition of Cultivation Media M1-M8

| | M1 | M2 | M3 | M4 | M5 | M6 | M7 | M8 |
|---|---|---|---|---|---|---|---|---|
| MS salt with B5 vitamins (PhytoTech M404) | 4.44 g/L | | 4.44 g/L | | | | 4.44 g/L | |
| Gamborg B-5 basal medium (PhytoTech G398) | | | | | | | | 3.21 g/L |
| Modified MS salt (PhytoTech M571) | | 2.68 g/L | | 2.68 g/L | 2.68 g/L | 2.68 g/L | | |
| B5 vitamins (1000X) (PhytoTech G249) | | 1 ml | | 1 ml | 1 ml | 1 ml | | |
| 2,4-D stock 10 mg/ml | 4 ml | 1 ml | | 1 ml | 1 ml | 1 ml | | |
| $KNO_3$ | | 0.93 g/L | | 0.93 g/L | 1.64 g/L | 1.64 g/L | | |
| $(NH_4)_2SO_4$ | | 0.463 g/L | | 0.463 g/L | 0.463 g/L | 0.463 g/L | | |
| Asparagine | | 1 g/L | | 1 g/L | 1 g/L | 1 g/L | | |
| Sucrose | | 10 g/L | | 10 g/L | 68.5 g/L | 85.6 g/L | | 20 g/L |
| Glucose | 31.5 g/L | | 30 g/L | | 36 g/L | 49.6 g/L | | |
| Sorbitol | | | | 45.6 g/L | | | | |
| Mannitol | | | | 45.6 g/L | | | | |
| Maltose | | | | | | | 60 g/L | |
| $MgCl_2 \cdot 6H_2O$ | | | | | | | 0.75 g/L | |
| Activated charcoal (PhytoTech C325) | | | | | | | 5 g/L | |
| Casein hydrolysate (PhotoTech C184) | | | | | 1 g/L | 1 g/L | | |
| pH | 7.0 | 5.8 | 5.4 | 5.4 | 5.4 | 5.4 | 5.7 | 5.7 |
| Acetosyringone | | 300 μM | 300 μM | 300 μM | 300 μM | 300 μM | | |
| TC agar | 4 g/L | | | | | | | 5 g/L |
| Gelrite (Plant Media Cat# 714246) | | | | 2 g/L | | | 2 g/L | |

Example 2

Agrobacterium and Plasmid

Agrobacterium tumefaciens AGL-1, EHA105, GV3101, and LBA4404 containing a binary plasmid were used. The binary plasmid contains the coding region for an intron-containing red fluorescent protein (DsRED) gene driven by the Arabidopsis UBQ10 promoter, hygromycin resistance under regulatory control of the CaMV35S promoter, and an intron-GM-HRA driven by the GM SAMS promoter in the T-DNA borders. Fluorescent proteins like DsRED, due to their intrinsic fluorescence, allow for noninvasive detection in living cells without the addition of substrates. This enables, for example, real time visualization of gene expression. Plasmid was introduced into Agrobacterium strains by electroporation and cultured on LB agar (10 g/L tryptone, 5 g/L yeast extract, 5 g/L NaCl, 8 g/L agar) plate containing 100 mg/L kanamycin at 28 C. Kanamycin-resistant colonies were grown in 100 mg/L kanamycin LB liquid medium and frozen glycerol stock cultures stored at −80° C. were prepared.

Example 3

Transformation and Plant Regeneration Procedures

The day before transformation, the A. tumefaciens from the glycerol stock was inoculated in a tube containing 5 ml of fresh LB liquid medium containing 100 mg/L kanamycin, then placed on a shaker incubator at 250 rpm overnight at 28° C. On the day of transformation, log phase A. tumefaciens AGL-1, EHA 105, GV3101 or LBA4404 cells containing the binary plasmid were centrifuged at 1,500×g for 10 minutes and resuspended in various liquid co-cultivation medium (M2, M3, M4, M5, and M6) as presented in Table 1. The Agrobacterium were then diluted to an OD600 nm of 0.3-0.5 with co-cultivation medium.

About 30-50 clumps of fresh green and compact soybean embryogenic callus (2-3 mm in size) were transferred to a sterile Petri dish. A volume of 10 ml of Agrobacterium suspension in co-cultivation medium containing 300 μM Acetosyringone (AS) was added to the embryogenic callus culture plate. Tissue in suspension was either wounded or not. Wounding techniques included using forceps to finely break up the tissues or fine chopping with the #11 blade (Feather Safety Razor Co., Osaka, Japan). The embryogenic callus tissues equivalent to about 30 clumps in co-cultivation medium was spread onto the sterile double layered filter paper (415, VWR International, West Chester, Pa., USA) evenly with cut pipette tips. The upper filter with embryogenic cultures was blotted onto new sterile filter paper to remove excess bacteria and put onto a new filter paper again. The plates were labeled and sealed with Parafilm® (Pechiney Plastic Packaging Company, Chicago, Ill.). Co-cultivation was carried out up to 5 days at 21° C. with an 18 hour photoperiod at 5-10 μE/m²/s light intensity. During the co-cultivation period, the levels of transient expression for DsRED fluorescent protein were observed under the Leica fluorescence stereomicroscope (Leica, Wetzlar, Germany) equipped with a filter set for excitation at 530-560 nm and emission at 590-650 nm and the extent of tissue viability were also observed.

After 1-5 days of co-culture, the embryogenic callus was collected from the filter papers and the tissue amount equivalent to 10 embryogenic callus clumps were transferred into the liquid recovery medium M2 containing 50 ml of 300 mg/l Timentin®, an antibiotic to kill off the *Agrobacterium* without selection. The embryos were cultured at 26° C. with 18 hour photoperiod at 60-80 µE/m$^2$/s light intensity for 7 days with the same shaking conditions described above in Example 1.

Following the recovery treatment, hygromycin or chlorosulfuron as selective agents were used for the selection of stable transformants. For hygromycin selection, the liquid media consisted of 50 ml of fresh M2 containing 15 mg/L hygromycin (CalBiochem, La Jolla, Calif., USA) and 300 mg/l Timentin® (PlantMedia, Dublin, Ohio, USA) for the first week and then 30 mg/L hygromycin and 300 mg/L Timentin® for the rest of selection period up to total 8 weeks of selection. For chlorosulfuron selection, with the *Agrobacterium*-infected tissue was incubated in 50 ml of fresh M2 containing 100 µg/L chlorosulfuron (Chem Service, West Chester, Pa., USA) and 300 mg/L Timentin® for the entire selection period which lasted up to total 8 weeks. The selective media was replaced weekly. After 6-8 weeks on selective medium, transformed tissue became visible as green tissue against a background of bleached, less healthy tissue. Putative transformed tissue was isolated under the microscope and inoculated into 6 well plates containing 5 ml of M2 medium with 30 mg/L hygromycin and 300 mg/L Timentin® or 100 µg/L chlorosulfuron and 300 mg/L Timentin® in each well. These pieces of tissue were incubated for an additional 4-8 weeks. Liquid medium was replaced weekly during this time.

Whole plants were then regenerated from the embryogenic callus propagated in liquid medium containing either hygromycin or chlorsulfuron. Green and healthy embryogenic callus clusters were removed from multi-well plate and spread onto M7 media solidified with agar and supplemented with 100 mg/L Timentin®. The Petri plates were sealed with Micropore™ tape (3M Health Care, St. Paul, Minn., USA) and incubated at 26° C. After 2 weeks, somatic embryos were transferred to M7 media without activated charcoal containing 100 mg/L Timentin®. After a total of 4 weeks on maturation on M7 media, mature somatic embryos were placed in sterile, empty Petri dish, sealed with Micropore™ tape (3M Health Care, St. Paul, Minn., USA) or placed in a plastic box (with no fiber tape) for 4-7 days at room temperature.

Desiccated embryos were planted in M8 media where they were left to germinate at 26° C. with 18 hour photoperiod at 60-100 µE/m$^2$/s light intensity. After 4-6 weeks in germination media, the plantlets were transferred to moistened Jiffy-7 peat pellets (Jiffy Products Ltd, Shippagan, Canada), and kept enclosed in clear plastic tray boxes until acclimatized in Percival incubator at conditions of 16 hour photoperiod at 60-100 µE/m$^2$/s, 26° C./24° C. day/night temperatures. Finally, hardened plantlets were potted in 2 gallon pots containing moistened SunGro 702 and grown to maturity, bearing seed, in a greenhouse.

Example 4

Co-Cultivation and Recovery Medium

The influence of various co-cultivation medium (Table 1) was evaluated on the level of DsRED transient expression and tissue viability following co-cultivation of the tissue with *Agrobacterium*. Log phase *A. tumefaciens* LBA4404 was resuspended in various liquid co-cultivation medium. Elite variety A soybean embryogenic callus was transformed with LBA4404 and co-cultivated by the filter paper method as described in Example 3. The tissue was co-cultivated with *Agrobacterium* for 3 days and DsRED expression was assayed 3 days after the end of the co-cultivation period. In M2 and M3 co-cultivation medium 3 days after transformation, the soy embryogenic cultures exhibited no DsRed expression (Table 2) and also showed tissue yellowing. No DsRED expression was observed even after extended co-cultivation period up to 4 days. On the other hand, tissue co-cultivation in M4, M5, and M6 medium, exhibited substantial levels of DsRED transient expression 2 days after transformation and displayed even higher expression 3 days after infection (Table 2). Even though high levels of DsRED expression was observed in tissue treated with M4 co-cultivation medium, the embryogenic callus displayed tissue yellowing in M4. In contrast, tissue co-cultivated in M5 and M6 medium were greener and healthier than tissue co-cultivated with M2, M3, and M4. Modified M4 medium adjusted to 0.93 g/L KNO$_3$ or with the removal of casein hydrolysate also showed good DsRED transient expression and tissue viability 3 days after infection as compared to M4 medium without these modifications. The results indicate that different combinations and concentrations of sucrose and glucose have a very important role for successful T-DNA transfer and tissue viability following co-cultivation with *Agrobacterium*. A successful co-cultivation period was 2 days. Co-cultivation periods longer than 3 days resulted in increased tissue necrosis and browning.

TABLE 2

The influence of co-cultivation medium on gene delivery by *Agrobacterium* to embryogenic callus tissue of soybean

| | M2 | M3 | M4 | M5 | M6 |
|---|---|---|---|---|---|
| DsRED transient expression (number of expressing cells/20 clumps of embryogenic callus)* | 0 | 0 | 1293 ± 577* | 740 ± 378 | 1905 ± 593 |

*Standard deviation

Figure 1:
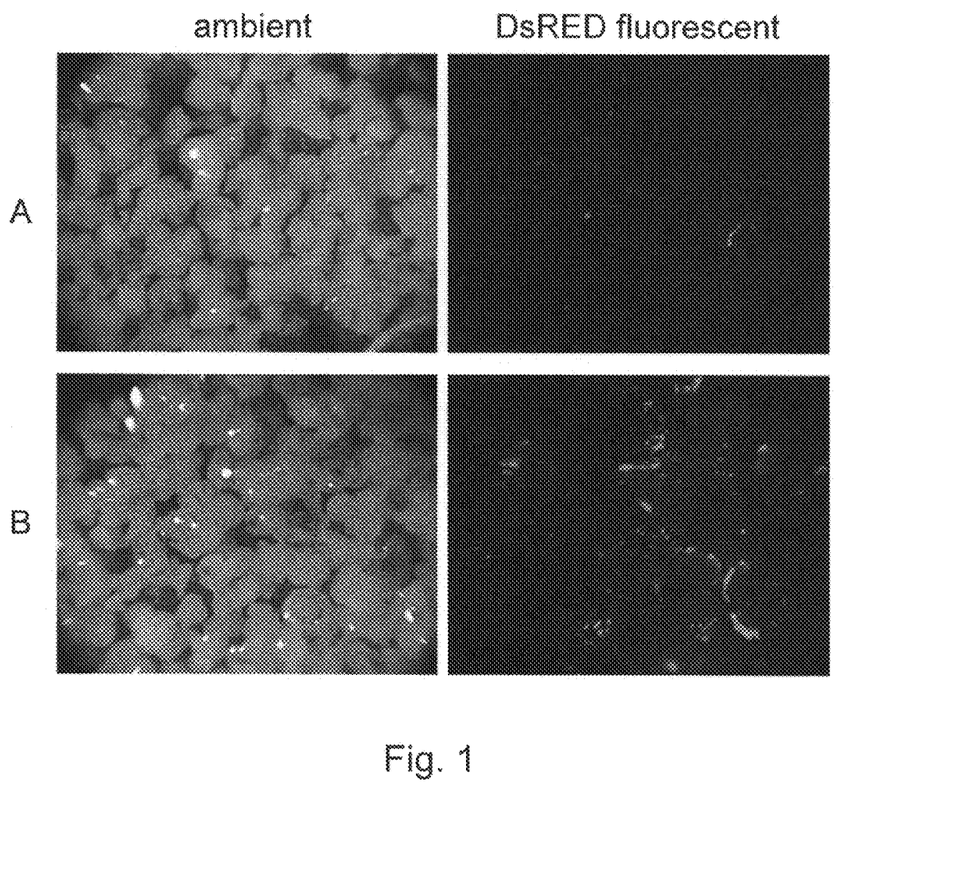
FIG. 1 depicts transient expression of DsRED resulting from co-cultivation in M5 medium as compared to that of M2 and M3 media.

Following co-cultivation for 2 days, the embryogenic callus was collected from the filter paper and cultured in M2 liquid medium containing 300 mg/L Timentin®, an antibiotic to eliminate the *Agrobacterium*. This phase of the transformation process (after treating the tissue with Timentin® and before treatment with the selective agent) was termed the tissue recovery phase. Embryogenic callus co-cultivated in the M2 and M4 liquid medium after 7 days suffered from yellowing/bleaching and most of tissues died. On the other hand, embryogenic callus co-cultivated in M5 medium showed much greener and healthier tissue after 7 days. In addition, as shown in Table 3, transient expression of DsRED resulting from co-cultivation in M5 medium (FIG. 1B) was significantly increased compared to that of M2 (FIG. 1A) and M3. DsRED expression was assayed 7 days after the end of the recovery period.

TABLE 3

The level of DsRED expression on M2 recovery medium followed by the treatment on the various co-cultivation medium

|  | M2 | M3 | M4 | M5 |
|---|---|---|---|---|
| DsRED transient expression (number of expressing cells/20 clumps of embryogenic callus) | 0 | 0 | 5400 | 27000 |

Example 5

Co-Cultivation on Filter Paper Vs. Semi-Solid Agar Vs. Liquid Medium

Elite variety A soybean embryogenic callus was transformed by *A. tumefaciens* AGL-1 (containing the binary plasmid) in M2, M4, and M5 co-cultivation medium with fine chopping treatment as described in Examples 3 and 7. Following treatment with the *Agrobacterium* suspension the tissue was transferred to either filter paper or semi-solid agar media using the following procedures. For co-cultivation onto filter paper, fine embryogenic callus equivalent to about 20 clumps was placed on the top layer of a stack of 2 pieces of filter paper. The upper filter paper with fine embryogenic callus was placed on top of a piece of fresh sterile filter paper to remove excess liquid and bacteria. The blotted filter with tissue was then transferred again to a fresh piece of sterile filter paper. For co-cultivation on semi-solid medium, fine embryogenic callus equivalent to about 20 clumps was placed on the top layer of a stack of 2 pieces of filter paper. The upper filter paper with fine embryogenic callus was placed on top of a piece of fresh sterile filter paper to remove excess liquid and bacteria. The blotted filter with tissue was then placed onto solid co-cultivation medium containing 6 g/L agar. The Petri dishes were sealed with Parafilm® and incubated for 3 days as described in Example 3.

For co-cultivation in liquid medium, about 20 clumps of fine embryogenic calli were placed on the top layer of a stack of 2 pieces of filter paper. The upper filter paper with fine embryogenic callus was placed on top of a piece of fresh sterile filter paper to remove excess liquid and bacteria. Fine embryogenic cultures equivalent to about 10 clumps were collected from the filter paper and transferred to 50 ml liquid co-cultivation medium containing 300 µM AS in 250 ml flasks. Liquid co-cultivation medium was replaced daily to reduce bacterial overgrowth. Table 4 shows that transient expression of DsRED was only observed from the filter paper method. DsRED expression was not observed after co-cultivation on M4 and M5 medium.

TABLE 4

Co-cultivation onto filter paper, semi-solid medium, and in liquid medium

| Co-cultivation | M2 | M4 | M5 |
|---|---|---|---|
| Filter paper | 0 | 1293 ± 577* | 744 ± 378 |
| Semi-solid medium | 0 | 0 | 0 |
| Liquid medium | 0 | 0 | 0 |

*Standard deviation

Example 6

*Agrobacterium* Strains

Four disarmed *Agrobacterium* strains were compared for their ability to mediate transformation of soybean embryogenic cultures. Elite variety A soy embryogenic cultures were transformed with *A. tumefaciens* AGL-1, EHA105, GV3101, and LBA4404 harboring the binary plasmid in M5 co-cultivation medium by the chopping treatment. Following 3 days of co-cultivation, T-DNA transfer to cells in the soybean embryogenic cultures was determined by observing DsRED transient expression. All four strains produced high level of transient DsRED expression but EHA105 showed the least expression level (data not shown). Of the strains tested, the preferred *Agrobacterium* strains were AGL-1, GV3101, and LBA4404. There was no significant difference of the tissue viability observed in four strains.

Table 5 shows stable transformation frequency of elite cultivar A transformed with *A. tumefaciens* AGL-1, GV3101 and LBA4404 harboring the binary plasmid after 8 weeks of selection with 30 mg/L hygromycin. Transgenic tissue was clearly identified by its green, healthy appearance as compared to surrounding dead tissue killed by hygromycin. Also, the transgenic tissue clearly expressed DsRED as indicated by observation using a microscope equipped with a fluorescent light source. All three strains produced stably transformed embryos and the transformation frequencies were 1.3% (AGL-1), 1.1% (GV3101), and 2.0% (LBA4404), respectively.

TABLE 5

Comparison of transformation frequency by *A. tumefaciens* strains

| Agrobacterium strain | Number of total clumps of embryogenic callus | Number of dsRED positive embryogenic events 8 weeks after selection | Transformation frequency % (Events per clump) |
|---|---|---|---|
| AGL-1 | 260 | 4 | 1.5 |
| GV3101 | 280 | 3 | 1.1 |
| LBA4404 | 250 | 5 | 2.0 |

Example 7

Wounding Effects on Co-Cultivation

Figure 2:
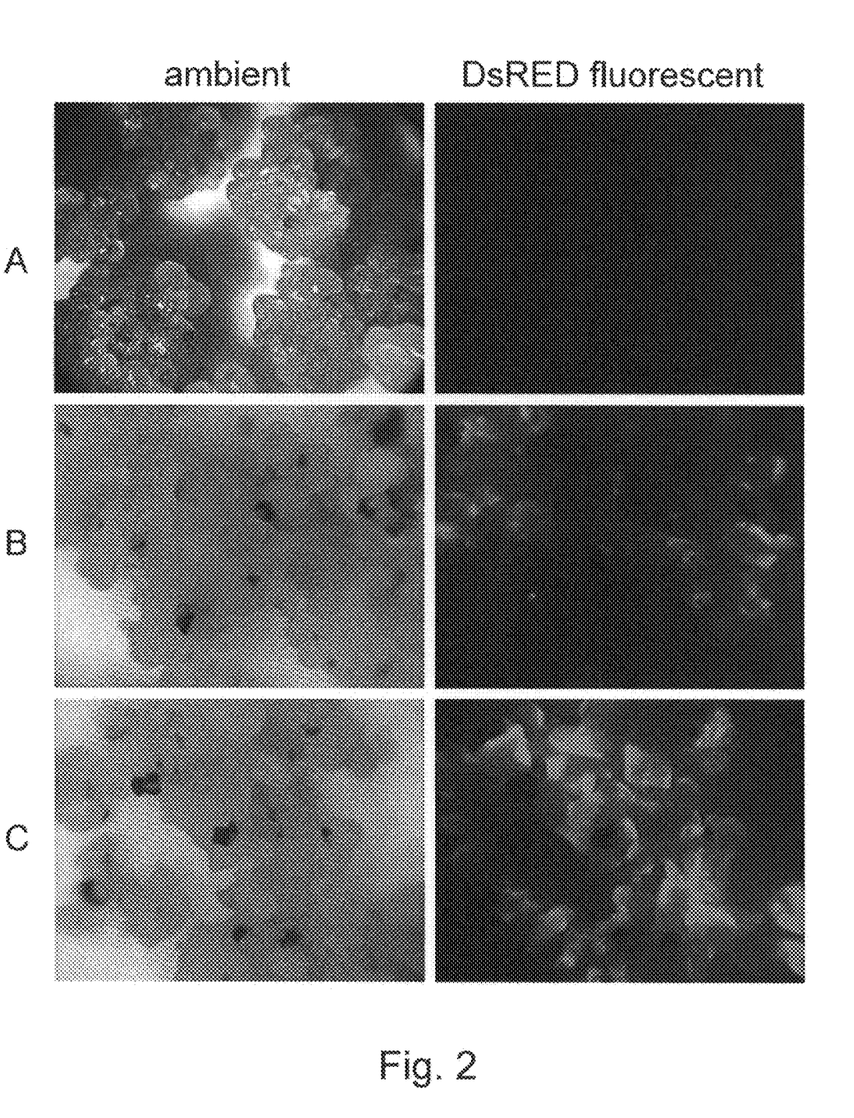
FIG. 2 depicts transient expression of DsRED in elite variety B embryogenic cultures transformed with LBA4404 (PHP40332) after 3 days of co-cultivation. Transient expression of DsRED was tremendously enhanced following *Agrobacterium* infection combined with breaking (B) or chopping (C) the soybean tissue as compared to that observed in non-wounded tissue (A).

To determine the effect of wounding treatments, elite variety B soybean embryogenic cultures with *A. tumefaciens* LBA4404 (having the binary plasmid) suspension in the M5 co-cultivation medium was treated with no wounding, fine breaking with forceps, or chopping with a #11 blade. After each treatment, the embryogenic cultures were co-cultivated onto filter paper. FIG. 2 shows transient expression of DsRED in elite variety B embryogenic cultures transformed with LBA4404 after 3 days of co-cultivation.

Transient expression of DsRED was not observed following *Agrobacterium* infection of cultures that were not wounded (FIG. 2A). However, when *Agrobacterium* was combined with breaking (FIG. 2B) or chopping (FIG. 2C) the soybean tissue, DsRED transient expression was tremendously enhanced compared to that observed in non-wounded tissue. Chopping the tissue produced higher levels of DsRed transient expression than breaking the tissue. This level of transient expression was roughly equivalent to or even higher than levels obtained using particle bombardment of the same target tissue. Same patterns of transient expression were observed from Jack and elite variety A embryogenic cultures transformed with *A. tumefaciens* AGL-1, EHA105, and GV3101 harboring the binary plasmid (data not shown).

Example 8

Response of Different Soybean Varieties

Jack, elite variety A, and elite variety B embryogenic cultures were co-cultivated with *A. tumefaciens* AGL-1 using the M5 co-cultivation medium. The tissue was treated with the fine breaking method and was placed onto double layer filter paper for co-cultivation. All three soybean varieties exhibited very high transient DsRED expression (data not shown). After 8 weeks of selection with hygromycin (30 mg/L), DsRED positive embryos were obtained in Jack, elite variety A and elite variety B cultures as shown in Table 6. The results presented show that all three soybean varieties tested can be transformed by *A. tumefaciens* and can produce stably transformed events using this method.

TABLE 6

Comparison of transformation frequency by soybean cultivars

| Cultivar | Number of total clumps of embryogenic callus | Number of dsRED positive embryogenic events 8 weeks after selection | Transformation frequency % (Events per clumps) |
|---|---|---|---|
| Jack | 420 | 60 | 14.3% |
| Elite variety A | 530 | 8 | 1.5% |
| Elite variety B | 240 | 3 | 1.3% |

Example 9

Selectable Markers

Figure 3:
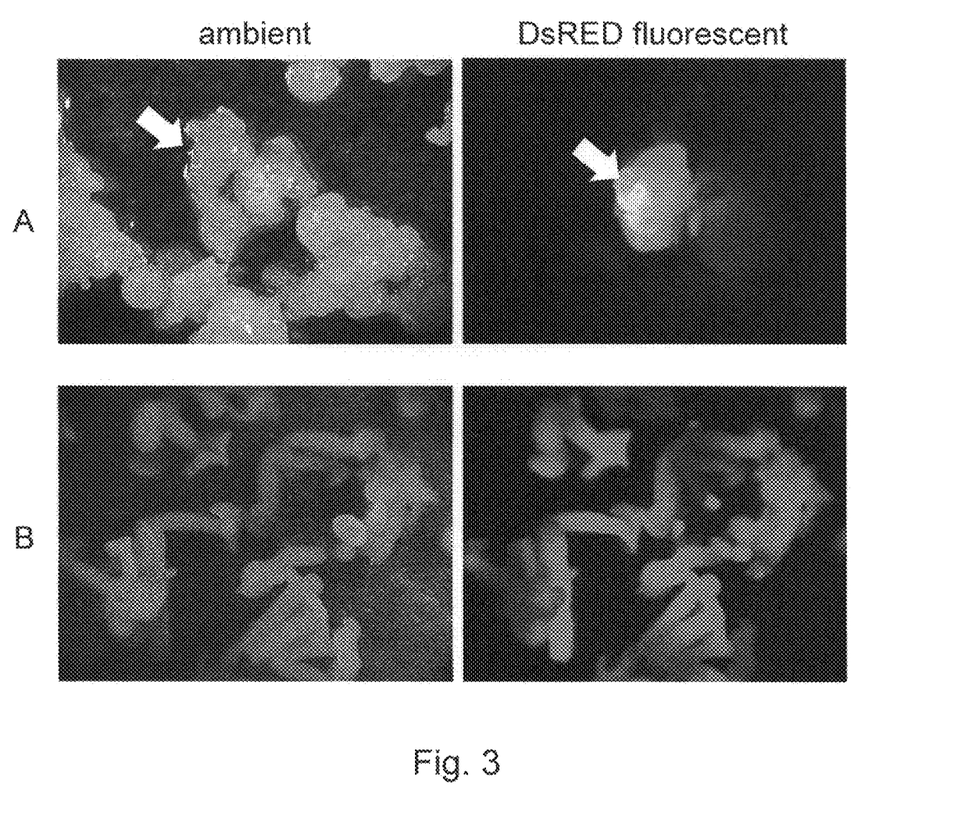
FIG. 3 depicts stably transformed events following hygromycin or chlorosulfuron selection.

Soybean Jack embryogenic cultures with *A. tumefaciens* LBA4404 suspension in the M5 co-cultivation medium was treated with fine breaking method and was placed onto the double layer filter paper for co-cultivation. After 8 weeks of 30 mg/L hygromycin or 100 µg/L chlorosulfuron selection, the green clumps of tissues that exhibited red fluorescence was identified (FIG. 3A). Transformation frequencies were 18.7% with hygromycin and 6.7% with chlorosulfuron (Table 7). Red fluorescence was detected throughout the matured somatic embryos under the fluorescence microscope (FIG. 3B) and many transformed embryos even expressed a light red phenotype even under ambient light. The results presented showed that either hygromycin or chlorosulfuron selection can produce stably transformed events using this method.

TABLE 7

Comparison of transformation frequency by selective agents

| Selection | Number of total clumps of embryogenic callus | Number of dsRED positive embryogenic events 8 weeks after selection | Transformation frequency % (Events per clumps) |
|---|---|---|---|
| Hygromycin 30 mg/l | 80 | 15 | 18.7% |
| Chlorosulfuron 100 ug/l | 60 | 4 | 6.7% |

Example 10

Sonication Treatments

To determine the effect of sonication treatments, soybean embryogenic cultures were treated with either chopping using a #11 blade (Example 7) or sonication. For sonication treatments, 15-20 clumps of elite variety B soybean embryogenic cultures (line 052110) were transferred to either sterile 13×100 mm glass tubes (VWR, 47729-572) or 25×250 mm glass tubes (47729-586) with respectively either 1 ml or 3-5 ml of OD 0.3 *A. tumefaciens* GV3101 (having the binary plasmid) suspension in M5 co-cultivation medium. The embryogenic cultures were suspended in this volume by mild agitation and placed in a float at the center of ultrasonic bath (VWR, Model 50T). The suspension cultures were sonicated for 0, 5, 10, 20, 30, 60, 90 or 120 seconds. After each treatment, the embryogenic cultures were co-cultivated onto double layer filter paper for 2-3 days and transient expression of DsRED was observed. Chopping the tissue produced higher levels of DsRed transient expression than sonicating the tissue but different expression patterns were observed. In chopped tissues most DsRED transient expression was observed in the cutting sites of the target tissue. On the other hand, transient expression in sonicated tissues was observed over the entire surface of tissues. The 30 second treatment gave the highest levels of transient expression while maintaining a high viability of the cells. Table 8 shows stable transformation frequency of elite cultivar B (line 052110) transformed with *A. tumefaciens* GV3101 harboring the binary plasmid after 8 weeks of selection with 30 mg/L hygromycin. Sonication treatment increased the transformation significantly in soybean embryogenic suspension cultures.

TABLE 8

Effect of sonication for 30 seconds

| Treatment | Number of total clumps of embryogenic callus | Number of dsRED positive embryogenic events 8 weeks after selection | Transformation frequency % (Events per clumps) |
|---|---|---|---|
| Chopping | 15 | 3 | 20% |
| Sonication in 13 × 100 mm tube | 15 | 10 | 66.7% |
| Sonication in 25 × 150 mm tube | 20 | 20 | 100% |

The same pattern of transient expression and increased transformation frequencies of stable events using sonication treatment conducted by two different researchers were observed with *A. tumefaciens* AGL-1, EHA105, GV3101, and LBA4404 harboring the binary plasmid (Table 9).

TABLE 9

Effect of *Agrobacterium* strain

| *Agro* Strains | #Tissue clumps | # Events | TE |
|---|---|---|---|
| Researcher 1 | | | |
| LBA4404* | 160 | 11 | 7% |
| EHA105* | 30 | 0** | 0% |
| GV3101* | 240 | 22 | 9% |
| AGL-1* | 100 | 5 | 5% |
| ALG-1 (chopping) | 100 | 2 | 2% |

TABLE 9-continued

Effect of *Agrobacterium* strain

| *Agro* Strains | #Tissue clumps | # Events | TE |
|---|---|---|---|
| Researcher 2 | | | |
| LBA4404* | 130 | 20 | 15% |
| GV3103* | 30 | 11 | 37% |
| AGL-1* | 60 | 8 | 13% |
| ALG-1 (chopping) | 100 | 2 | 2% |

*sonicated
**contaminated - no events

Example 11

Molecular Analyses

Quantitative polymerase chain reaction (qPCR) for putative events of Jack matured embryos was done using primers for the PINII terminator, 35S promoter, and SAMS promoter. qPCR reactions were followed by the manuals from Applied Biosystems (Life Technologies Corporation, Carlsbad, Calif., USA) for real-time qPCR machine 7500 and 7900HT. A total of 41 Jack events analyzed presented the probability of qPCR Positive Events containing at least one copy for all three genes respectively was 100% (Table 10). In addition, the efficiencies of qPCR Single Copy Events for all three genes were 66%. *Agrobacterium*-mediated transformation typically gives rise to lower transgene copy number, when compared to direct transformation method.

TABLE 10 qPCR for putative events of Jack matured embryos after selection with hygromycin 30 mg/L or 100 µg/L chlorosulfuron

| Copy Number | PINII | % | 35S | % | SAMS | % |
|---|---|---|---|---|---|---|
| 0 | 0 | 0 | 0 | 0 | 0 | 0 |
| 1 | 30 | 73 | 31 | 76 | 27 | 66 |
| 2 | 8 | 20 | 5 | 12 | 8 | 20 |
| 3 | 3 | 7 | 1 | 2 | 1 | 2 |
| >3 | 0 | 0 | 4 | 10 | 5 | 12 |
| Total | 41 | 0 | 41 | 0 | 41 | 0 |

Example 12

Fertile Plant Regeneration

Stably transformed soybean plants from Jack and elite cultivars were regenerated, successfully transplanted to soil, and grown in the greenhouse. The method presented generally enables the production of transgenic plants within about 6 months from the initiation of transformation to transferring plantlets to soil. Even though the variation of plant fertility were observed frequently, many transformed plants expressing DsRED from embryogenic cultures less than 4-5 month old from initiation were fertile and T1 progeny was recovered. Some T1 seeds from self-pollinated T0 plants showed a red color even under ambient light and appeared to grow in a manner similar to that of nontransgenic soybean. Indeed, it was possible to segregate T1 seeds visually on the basis of the absence or presence of DsRed2 fluorescence. On the other hand, untransformed Jack seeds showed no visible red color at all. The results presented show that fertile transgenic soybean plants can be produced using this method References cited within this application, including patents, published applications and other publications are herein incorporated by reference.

Although the foregoing invention has been described in some detail by way of illustration and example for purposes of clarity of understanding, it will be obvious that certain changes and modifications may be practiced within the scope of the appended claims.

That which is claimed:

1. A cultivation medium for *Agrobacterium*-mediated transformation comprising high levels of sucrose and glucose, wherein the cultivation medium comprises about 10 to about 100 grams/Liter sucrose, about 20 to about 75 grams/Liter glucose, about 2.4 grams/Liter to about 3.9 grams/Liter potassium nitrate ($KNO_3$), about 0.2 grams/Liter to about 0.6 grams/Liter ammonium sulphate (($NH_4$)$_2SO_4$), and about 1 gram/Liter asparagine.

2. The cultivation medium of claim 1, wherein said sucrose is present at about 68 grams/Liter and glucose is present at about 36 grams/Liter.

3. The cultivation medium of claim 1, comprising about 68 grams/L sucrose, about 36 grams/L glucose, about 3.5 grams/L potassium nitrate ($KNO_3$), about 0.5 grams/L ammonium sulphate (($NH_4$)$_2SO_4$), and about 1 gram/L asparagine.

* * * * *